(12) United States Patent
Huber et al.

(10) Patent No.: US 9,072,340 B2
(45) Date of Patent: Jul. 7, 2015

(54) LOWER LIMB ORTHOSIS

(75) Inventors: David Huber, Austinmer (AU); Craig Andrews, Mosman (AU)

(73) Assignee: GUARDAHEEL IP PTY LIMITED (AU)

( * ) Notice: Subject to any disclaimer, the term of this patent is extended or adjusted under 35 U.S.C. 154(b) by 816 days.

(21) Appl. No.: 12/935,064

(22) PCT Filed: Mar. 30, 2009

(86) PCT No.: PCT/AU2009/000381
§ 371 (c)(1),
(2), (4) Date: Dec. 23, 2010

(87) PCT Pub. No.: WO2009/121121
PCT Pub. Date: Oct. 8, 2009

(65) Prior Publication Data
US 2011/0099851 A1    May 5, 2011

(30) Foreign Application Priority Data
Mar. 31, 2008  (AU) ................. 2008901538

(51) Int. Cl.
*A47B 7/00* (2006.01)
*A43B 13/16* (2006.01)
*A43B 7/14* (2006.01)
(Continued)

(52) U.S. Cl.
CPC ............... *A43B 13/16* (2013.01); *A43B 7/144* (2013.01); *A43B 7/141* (2013.01); *A43B 7/142* (2013.01); *A43B 7/143* (2013.01); *A43B 7/1445* (2013.01); *A43B 17/026* (2013.01); *A61F 5/0111* (2013.01)

(58) Field of Classification Search
CPC ...... A43B 7/144; A43B 7/141; A43B 7/1425; A43B 7/1465; A43B 7/20
USPC ........... 5/624, 648, 651, 731, 734; 36/71, 140
See application file for complete search history.

(56) References Cited

U.S. PATENT DOCUMENTS 1,945,780 A    2/1934  Johnson
3,256,879 A *  6/1966  Hipps ........................... 128/892
(Continued)

FOREIGN PATENT DOCUMENTS

CA    2167865 A1    8/1996
WO    03/090573 A1    11/2003

OTHER PUBLICATIONS

International Preliminary Report on Patentability, PCT International Application No. PCT/AU2009/000381, dated Mar. 3, 2009.
(Continued)

*Primary Examiner* — Robert G Santos
*Assistant Examiner* — Myles Throop
(74) *Attorney, Agent, or Firm* — J.A. Lindeman & Co., PLLC

(57) ABSTRACT

An above heel lower limb orthosis comprising: an orthosis body; a support surface adapted to support a portion of a lower limb, the support surface connected to, secured to, or integral with the orthosis body; relief means adapted to relieve a portion of a lower limb from pressure; and at least one relief region connected to, secured to, or integral with the orthosis body or the support surface or the orthosis body and the support surface, the relief region depressed relative to the support surface and adapted to receive, secure, or integrate the relief means.

19 Claims, 13 Drawing Sheets

(51) Int. Cl.
*A43B 17/02* (2006.01)
*A61F 5/01* (2006.01)

(56) References Cited

U.S. PATENT DOCUMENTS

| | | | |
|---|---|---|---|
| 3,777,419 A | 12/1973 | Nalick | |
| 3,859,740 A * | 1/1975 | Kemp | 36/71 |
| 4,168,585 A | 9/1979 | Gleichner | |
| 4,290,155 A * | 9/1981 | Hanson | 5/722 |
| 4,482,138 A * | 11/1984 | Spann | 5/648 |
| 4,602,626 A | 7/1986 | Johnson | |
| 5,067,256 A | 11/1991 | Darby | |
| 5,997,491 A * | 12/1999 | Harris | 602/6 |
| 6,155,998 A * | 12/2000 | Gilmour | 602/27 |
| 6,990,756 B1 | 1/2006 | Johnson | |
| 7,380,352 B2 * | 6/2008 | Seiter | 36/44 |
| 7,581,266 B2 * | 9/2009 | Krecow et al. | 5/624 |
| 2004/0092853 A1 * | 5/2004 | Degun et al. | 602/27 |
| 2005/0150133 A1 | 7/2005 | Khoury | |
| 2006/0150983 A1 * | 7/2006 | Huber et al. | 128/845 |
| 2007/0039208 A1 * | 2/2007 | Bove et al. | 36/97 |
| 2007/0079532 A1 * | 4/2007 | Ramirez | 36/140 |
| 2009/0227927 A1 * | 9/2009 | Frazer | 602/27 |

OTHER PUBLICATIONS

International Search Report, PCT International Application No. PCT/AU2009/000381, dated May 14, 2009.

* cited by examiner

LOWER LIMB ORTHOSIS

TECHNICAL FIELD

The present invention is broadly directed to orthoses. More specifically, the present invention is directed to above heel lower limb orthoses with associated or integrated relief means, and more specifically still, to above heel lower limb orthoses with associated or integrated relief means, and to related devices and methods.

BACKGROUND

There are a wide variety of orthoses available worldwide, with each orthosis having its own particular features to improve the comfort of a user and/or to aid in supporting a body part to which the orthosis is applied.

A number of generic problems tend to be experienced by orthoses users, and solutions to resolve some such problems are typically simplistic and may not fully address those problems for the longer term. For example, a central problem with orthoses derives from the fact that weight-bearing areas tend to experience increases in pressure, associated discomfort, and sometimes, tissue damage and/or bruising.

A number of orthoses have been used in the treatment and/or prevention of pressure ulcers, particularly pressure ulcers occurring on or around the heel and/or ankle. One of the more commonly used devices is a gel block which is placed under the Achilles tendon of a subject lying supine on a surface, such as a bed or operating theatre table. Examples of these gel blocks include the Action® Heel Support Model 40502 by Action Products, Inc., the Oasis Elite™ Heel Pad by the Trulife® Group and the AliGel™ Heel Cup by AliMed Inc.

While these (and other, like) gel blocks can support a subject's lower limb so that those areas which typically develop pressure ulcers in the region of, for example, the lateral malleolus and the calcaneus, they can create a number of other issues. For example, because the subject's lower limb may be immobile and therefore weight-bearing on the gel cushion for a prolonged period, such as, for example, during an operative procedure, an undesirable amount of pressure can be applied to the anatomical region adjacent or surrounding the Achilles tendon.

Also, placing an object, such as a block, under the Achilles tendon when a subject is supine on a surface can cause the knee to hyperextend. It is believed by the present inventors that hyperextension of the knee results in popliteal vein compression which may give rise to deep vein thrombosis.

The present inventors have now developed an improved orthosis.

SUMMARY OF THE INVENTION

According to a first aspect, the present invention provides a lower limb orthosis comprising:
an orthosis body;
a support surface adapted to support a portion of a lower limb, the support surface connected to, secured to, or integral with the orthosis body;
relief means adapted to relieve a portion of a lower limb from pressure; and
at least one relief region connected to, secured to, or integral with the orthosis body or the support surface or the orthosis body and the support surface, the relief region adapted to receive, secure, or integrate the relief means.

In a preferred embodiment, the relief means relieves from pressure a first portion of the lower limb and the support surface supports a second portion of the lower limb. Preferably, the first portion of the lower limb is the anatomical region adjacent and/or surrounding the Achilles tendon, and the second portion of the lower limb is the anatomical region adjacent and/or surrounding the bellies of the gastrocnemius and soleus muscles.

In use, the relief means and the support surface preferably substantially contour the same or different portions of the lower limb. In preferred embodiments, the relief means is connected to, secured to, or integrated with the relief region in a manner so that the support surface and a relief surface of the relief means contour an underside of the lower limb, and more preferably still, so that the support surface and the relief surface are adjacent each other. In one such preferred embodiment, the support surface and the relief surface contour the anatomical regions adjacent and/or surrounding the bellies of the gastrocnemius and soleus muscles and the Achilles tendon.

In use, the lower limb preferably rests on the orthosis which is on a surface in a resting plane, such as the surface of a bed. As a matter of practicality, in such embodiments, the orthosis passively exerts a pressure on the lower limb in response to the weight of the lower limb resting on the orthosis. Preferably, the physical configuration of the support surface and the relief means or of the support surface, the relief means and the relief region, is such that, in use, the pressure passively exerted by the orthosis on the lower limb is substantially evenly distributed along a length of the lower limb which comes into contact with the orthosis.

In preferred embodiments, the orthosis is an above heel orthosis.

In some preferred embodiments, the support surface has a longitudinal axis and at least a portion of a cross-section of the support surface is arcuate and concave. Preferably, this portion of the cross-section is adapted to support the anatomical region adjacent and/or surrounding the bellies of the gastrocnemius and soleus muscles.

In other preferred embodiments, the support surface can have alternate shapes and/or configurations of any kind provided they enable the support surface to support the anatomical region of the lower limb which the orthosis is being used to support. The support surface may be uniform, varying, or may include, for example, undulations or perforations. It may also have any one of a number of varying creases, lumps, depressions or crevasses which may be incorporated into the support surface to better accommodate the anatomical region which the support surface is adapted to support.

In some preferred embodiments, the support surface is substantially planar. Some such embodiments allow, in use, lateral and rotational movement, relative to the orthosis, of at least those parts of the lower limb supported by the support surface. Some embodiments of the substantially planar support surface include a wall portion on or adjacent one or both sides of the support surface. The wall portion preferably extends away from the support surface and, in use, provides means for inhibiting the lower limb from rolling-off or dislodging from the orthosis. In some such embodiments, there is a wall portion on or adjacent each side of the support surface and at least a part cross-section of the support surface including wall portions is a 'U'-like shape, and in some such preferred embodiments, the 'U'-like shape is shallow.

In some preferred embodiments, in use, the lower limb rests on the orthosis and is not gripped, substantially circumscribed or substantially encircled by the support surface or the orthosis.

The support surface of preferred embodiments may be connected to, secured to or integrated with, the orthosis body. The preferred mechanisms for connecting and/or securing the support surface to the orthosis body are various. In one preferred embodiment, for example, an underside of the support surface includes a clipping means, and an upper side of the orthosis body includes a corresponding clip receiving means. Engagement of the clipping means with the corresponding clip receiving means results in connection and/or securing of the support surface to the orthosis body. In another embodiment, the support surface can be connected and/or secured to the orthosis body by velcro, double-sided adhesive, glue, screws, rivets or any other securing means for effecting connection and/or securing as desired.

In particularly preferred embodiments, the support surface is integral with the orthosis body. In some such embodiments the support surface and orthosis body are formed from a single integral material which can be produced from, for example, a suitably shaped mould. In other such embodiments, the support surface and the orthosis body are formed from the same or different materials but are integrated together into a single unit. In one preferred embodiment, the relief region is depressed relative to, or 'carved-out' of, the support surface. In another preferred embodiment, a portion of a shape of the relief means corresponds to at least a portion of a shape of the relief region.

In some preferred embodiments, a length of the support surface is shorter than a length of the orthosis. In one preferred embodiment, the length of the support surface is such that, in use, the support surface spans from adjacent and distal the popliteal fossa to adjacent and proximal the origin of the Achilles tendon.

There may be one or more relief regions formed integrally with the support surface and/or the orthosis body or connected or secured to the support surface and/or the orthosis body. Relief regions are preferably positioned so as to accommodate relief means in the vicinity of locations where the lower limb is likely to experience increased pressure or discomfort when the orthosis is in use. For example, in a preferred embodiment, the relief region is located in the vicinity of the location where the anatomical region adjacent and/or surrounding the Achilles tendon is likely to rest or weight-bear on the orthosis in use.

In another preferred embodiment, the relief region is depressed relative to the orthosis body and/or the support surface. This depression is adapted so that at least a portion of the relief region can receive, secure or integrate a relief means. Some of the preferred mechanisms by which the relief region can receive or secure a relief means are similar to the mechanisms described above for the manner in which the support surface can be connected or secured to the orthosis body. For example, the relief means may be secured to the relief region using a double-sided adhesive interposed between the relief means and the relief region. In some such embodiments, the double-sided adhesive may be placed so as to substantially follow a perimeter of the relief means or may be placed substantially centrally to the surface area of the relief means. In other embodiments, the double-sided adhesive or other suitable mechanism is placed in a different location or configuration.

Some other preferred mechanisms in which the relief means can be received by or secured to the relief region are described below.

The relief region of some preferred embodiments includes a relief region surface. Preferably, the relief region surface is planar and has a longitudinal axis that runs substantially parallel a longitudinal axis of the support surface. In other preferred and alternative embodiments, there is an angle between a longitudinal axis of the relief region surface and a longitudinal axis of the support surface.

In one preferred embodiment wherein the relief region is depressed relative to the support surface and/or the orthosis body, and the longitudinal axes of the relief region surface and support surface are substantially parallel, the relief region surface 'steps-down' in physical configuration relative to the support surface.

Other surface features for the relief region surface include, but are not limited to, variegated, undulating, rough or smooth or a combination of these. In some preferred embodiments, the relief region surface is adapted to receive, secure, or integrate a relief means.

In yet still further preferred embodiments, the relief region includes a channel or void for receiving a relief means or a portion of the lower limb.

In some preferred embodiments, an end of the relief region and/or an end of the orthosis body and/or an end of the relief means has a functional width adapted so that, in use, the lower limb is aided in remaining supported by the orthosis despite voluntary or involuntary movement of the lower limb, or of other parts of the body which result in corresponding movements of the lower limb. For example, when a subject is supine on a surface, one or both lower limbs have a tendency, particularly at the ankle, to evert or externally rotate. The functional width of the end of the orthosis body or of the end of the relief region or of the end of the relief means or of two or more of the ends of the orthosis body, the relief region or the relief means will, in use, aid in retaining the lower limb supported by the orthosis despite such eversion at the ankle. Preferably, this or these functional width/s is/are on or adjacent the end on, or in the vicinity of which, in use, the Achilles tendon rests.

In other preferred embodiments, the physical configuration of the support surface and the relief region or of the support surface and the relief means is such that, in use, the lower limb is aided in remaining supported by the orthosis despite voluntary or involuntary movement of the lower limb. In one such embodiment, for example, the support surface is substantially planar and the relief region and/or relief means has a functional width at or adjacent the end on, or in the vicinity of which, in use, the Achilles tendon rests. This embodiment of the orthosis has an essentially open or generally planar area on which, in use, the lower limb rests. In a preferred configuration of this embodiment, there are no straps or other securing means to secure or hold the orthosis to the lower limb and the lower limb remains supported by the orthosis despite some voluntary or involuntary movements of the lower limb or of other parts of the body which result in corresponding movements of the lower limb.

In another preferred embodiment, the relief region includes an aperture into which a correspondingly shaped extending member or, for example, nozzle member, of the relief means can pass. As the extending member or, for example, nozzle member, extends beyond the aperture a clip means or connection member can be used to secure the relief means in place so that it is received by or secured to the relief region. In another embodiment, the extending member or, for example, nozzle member, is of a size and shape which expands, or is of a size and shape which has a portion which expands, when it (or a part of it) has passed through, and extended beyond an aperture. In such embodiments, the extending member or, for example, nozzle member, acts as a lug to keep the relief means received by or secured to the relief region.

In another preferred embodiment, the relief region integrates the relief means.

The relief means of some preferred embodiments is preferably formed from one or more materials selected from the group consisting of low density foam, high density foam, open cell and closed cell foams, rubber, solid or semi-solid gels and a combination of two or more thereof. The relief means of other preferred embodiments can be formed of any suitable material, whether natural or synthetic.

In yet still further preferred embodiments, the relief means may be formed of one or more pliable enclosures, with each pliable enclosure adapted to receive, hold or expel relief means density content. The relief means density content of some preferred embodiments may be selected from the group consisting of air, gas, gel, water, liquid, beads, foam particles or pieces, feathers, pulses or seeds of any kind, and a combination of two or more thereof. The relief means density content of other preferred embodiments, can be formed of any suitable material, whether natural or synthetic.

The relief means may also be formed of a combination of the material identified above and of one or more pliable enclosures. Some embodiments enable variation in the density of the relief means.

In another embodiment, the relief means takes the form of a suspended support, like a hammock-type support. In one form of this embodiment, the relief means is adapted to be suspended on or in connection with the orthosis so as to provide support to at least a portion of the lower limb. In one such embodiment, the suspended support is suspended above a channel or void in, or in association with, the relief region.

In further preferred embodiments, the relief means has a shape and/or configuration which substantially corresponds to a shape and/or configuration of at least a portion of the relief region of the orthosis.

Preferably, at least a portion of the relief means is configured so as to contour at least a portion of the relief region when the relief means is located on or in the vicinity of the relief region. In one preferred embodiment, for example, the relief means is key shaped and is adapted to contour at least a portion of the relief region which is correspondingly shaped. In another preferred embodiment, the relief means is a composite shape made up of two or more shapes, such as, for example, a rectangle adjacent a semi-circle or a rectangle adjacent a part-circle, greater in area than a semi-circle with the same diameter. In such embodiments, the semi-circle or part-circle is adjacent to a short side of the rectangle and in other embodiments, the semi-circle or part-circle is adjacent the longer side of the rectangle.

The diameter of the semi-circle or the part-circle may be equal to, shorter than or longer than the length of the side of the rectangle to which it is adjacent. In a particularly preferred embodiment, the shape of the relief means is comprised of a part-circle, greater in area than a semi-circle with the same diameter, adjacent a long side of a rectangle, wherein the diameter of the circle is shorter than the long side of the rectangle and the meeting point of the circumference of the part-circle with the long side of the rectangle is smooth and curved.

In another embodiment, the relief means is adapted to be inserted into a substantially correspondingly shaped slot-type structure formed in an end of the orthosis body adjacent the relief region and/or in the relief region itself. In embodiments, wherein the slot-type structure is formed in the end of the orthosis body, the structure opens into the relief region thereby enabling the relief region to receive, secure, or integrate a relief means.

In other preferred embodiments, the relief means can be of any particular shape and may or may not contour at least a portion of the relief region.

In one preferred embodiment, the relief means is formed from a pliable enclosure. The pliable enclosure is preferably formed of one or more materials selected from the group consisting of polyurethane, resins, elastomers, polymers, copolymers, pliable plastics, leather, rubber and a combination of two or more thereof. The pliable enclosure of other preferred embodiments can be formed of any suitable material, whether natural or synthetic.

In some preferred embodiments, the pliable enclosure contains pressure relief content selected from the group consisting of air, gas, gel, water, liquid, beads, foam particles or pieces, feathers, pulses or seeds of any kind, and a combination of two or more thereof. The pressure relief content of other preferred embodiments, can be formed of any suitable material, whether natural or synthetic.

In some preferred embodiments, the pliable enclosure has a closable opening adapted to allow or expel pressure relief content. The pressure relief provided by the relief means is preferably adjustable by allowing or expelling pressure relief content as desired.

In an alternative embodiment, the relief region opens into a cavity. The cavity may extend into the orthosis body. Preferably, the opening is spanned by a pliable material on which, in use, one anatomical region sought to be relieved from pressure rests. In this embodiment, pressure relief content may be added or injected to substantially fill the cavity until it supports an underside of the pliable material, thereby providing relief means. In a preferred embodiment, the opening is formed adjacent an end of the orthosis on or adjacent to which, in use, the anatomical region adjacent or surrounding the Achilles tendon rests.

In one preferred embodiment, at least a portion of the relief means is connected to, secured to, or integral with, at least a portion of the relief region. In another preferred embodiment, the relief means is removable from the relief region.

The relief means of some preferred embodiments is removable, replaceable and/or disposable. Such embodiments of the relief means are replaceable for each instance or period of use of the orthosis for the same subject or for a plurality of different subjects.

In further preferred embodiments, the relief means includes a liner element. The liner element is preferably integral with, connected or secured to, or rests on the relief means. In some preferred embodiments, the liner element substantially lines or covers a relief surface of the relief means. In other preferred embodiments, the liner element also extends away from the relief means thereby providing a flap-like structure for substantially lining or covering other parts of the orthosis or the lower limb. Preferably, the flap-like structure substantially lines or covers the support surface.

The liner element of preferred embodiments is formed from a material selected from the group consisting of surgical crepe material, vinyl, plastic, polypropylene, cotton and a combination of two or more of these materials.

In some particularly preferred embodiments, in use, the lower limb orthosis is adapted to aid in reducing the incidence of pressure ulcer formation in a subject. Preferably, the pressure ulcers, the incidence of which the lower limb orthosis is adapted to aid in reducing, include those which may form on or adjacent the anatomical region of the lateral malleolus and the calcaneus.

In some particularly preferred embodiments, in use, the orthosis is adapted to aid in elevating the heel above a surface in a plane of rest, such as the surface of a bed, preferably such that the anatomical regions adjacent and/or surrounding the calcaneous and lateral malleolus are relieved from pressure, and more preferably still, such that one or both of those anatomical regions are inhibited from making contact with the surface.

In some such embodiments, the lower limb orthosis is adapted to be placed on or adjacent an underside of the subject's lower limb substantially interposed between the anatomical regions of the popliteal fossa and the calcaneus. Preferably, the orthosis is adapted so that, in use, the orthosis does not come into contact with the anatomical region adjacent or surrounding the popliteal fossa, and more preferably, so that the orthosis does not apply any pressure to the anatomical region adjacent or surrounding the popliteal fossa. More preferably still, the orthosis is adapted so that, in use, the orthosis inhibits pressure from being applied to the anatomical region adjacent or surrounding the popliteal fossa by the orthosis or another object that may be located in the vicinity of the anatomical region adjacent or surrounding the popliteal fossa, such as, for example, a mattress, cushion, support or bed linen.

An end portion of the orthosis body of the lower limb orthosis of such embodiments which, in use, is located adjacent the popliteal fossa may be referred to as the proximal end portion of the orthosis. A substantially opposite end portion to the proximal end portion may be referred to as the distal end portion.

In some preferred embodiments, in use, the proximal end portion of the orthosis lies short of the popliteal fossa.

Preferably, in use, the lower limb orthosis is adapted to support the lower limb above a surface on which the lower limb is positioned such that the heel and ankle remain free of contact with the surface.

The orthosis body of preferred embodiments can be of any shape and/or configuration which is suitable to enable a lower limb to be supported and a support surface to be connected to, secured to or integral with, the orthosis body, and in some embodiments, a relief region to be connected to, secured to or integral with, the orthosis body.

The orthosis body of some preferred embodiments is preferably formed from one or more materials selected from the group consisting of low density foam, high density foam, open cell and closed cell foams, rubber, solid or semi-solid gels and a combination of two or more thereof. The orthosis body of other preferred embodiments can be formed of any suitable material, whether natural or synthetic.

In yet still further preferred embodiments, the orthosis body may be formed of one or more pliable enclosures, with each pliable enclosure adapted to receive, hold or expel orthosis body density content. The orthosis body density content of some preferred embodiments, may be selected from the group consisting of air, gas, gel, water, liquid, beads, foam particles or pieces, feathers, pulses or seeds of any kind, and a combination of two or more thereof. The orthosis body density content of other preferred embodiments, can be formed of any suitable material, whether natural or synthetic. The orthosis body may be formed of a combination of the material identified above and of one or more pliable enclosures. Some embodiments enable variation in the density of the orthosis body.

In one preferred embodiment, the orthosis body includes wing members adapted to extend in a manner that provides a channel in which the support surface can be located. The channel of such embodiments could also assist in supporting the lower limb and, in some embodiments, inhibit the lower limb from dislodging or rolling-off the orthosis when the lower limb moves (as, for example, under the volition of the person) or is moved (as, for example, by a surgeon or other healthcare worker during an operative procedure).

In other preferred embodiments, the orthosis body may include one or more hollowed portions. Such hollowed portions can reduce the volume of material required to manufacture the orthosis and/or orthosis body and can reduce the overall weight of the orthosis.

The hollowed portions of preferred embodiments can also be adapted to accommodate other objects or items, and in some preferred embodiments, can be used to decrease the rigidity of the orthosis body in the region of the hollowed portion. Such a reduction in rigidity may be associated with a corresponding increase in flexibility, thereby enabling limited movement of the orthosis in various parts so as to accommodate changes in weight, pressure or position of the lower limb with which the orthosis is being used.

In one preferred embodiment described above, wherein the relief region includes an aperture for receiving a correspondingly shaped extending member or nozzle member of the relief means, the orthosis body includes a hollowed portion adjacent the relief region, and the aperture through the relief region opens into the hollowed portion. In this embodiment, the clipping means or other means or member adapted to connect or secure the relief means to the relief region by securing the extending member or nozzle member as it extends out of the aperture, is placed to perform its function via a hollowed portion in the orthosis body.

The orthosis body of some preferred embodiments includes a base region. Preferably, the base region is adapted to at least partially come into contact with a resting surface, such as a bed or operating theatre table, when the orthosis is in use. The base region may also include an opening which opens into a hollowed portion. This is the case, for example, in the embodiment described in the preceding paragraph wherein the clipping means securably retains the extending member or nozzle member through the aperture. In that embodiment, the clipping means is securably connected to the extending member or nozzle member via the opening in the base region.

The base region or parts of the base region in some preferred embodiments further include a stabilising surface adapted to facilitate stabilisation of the orthosis on a resting surface, such as a bed or operating theatre table, when in use. The stabilising surface may comprise a rubberised portion or segment adapted to inhibit the orthosis from slipping or moving around on or relative to the resting surface and/or to substantially withstand movement forces that may be imposed on the orthosis by voluntary or involuntary movements of the lower limb. In one preferred embodiment, the entire base region is rubberised and in another preferred embodiment at least one part of the base region is rubberised.

The invention envisages a wide range of other means to enable the stabilising surface to perform its preferred function. For example, in one embodiment, the stabilising surface includes engagement means adapted to engage the resting surface or an interengagement member associated or integral with, connected to, or placed on or in association with, the resting surface. The engagement means may take the form of a slot or orifice adapted to receive the correspondingly shaped interengagement member. Operable engagement of the engagement means with the interengagement member assists in inhibiting the orthosis from slipping or moving around on or relative to the resting surface and/or substantially withstanding movement forces that may be imposed on the orthosis by voluntary or involuntary movements of the lower limb.

In another embodiment, the base region is weighted so as to substantially withstand movement forces that may be imposed on the orthosis by voluntary or involuntary movements of the lower limb. Such weighting can, in preferred embodiments, additionally or alternatively assist in inhibiting the orthosis from slipping or moving around on or relative to the resting surface.

In some preferred embodiments of the lower limb orthosis, particularly those adapted for use on the underside of the lower limb, anti-hyperextension means is connected to, secured to or integrated with the orthosis. In some such embodiments, the base region may additionally or alternatively integrate, engage or support the anti-hyperextension means. In other preferred embodiments, the anti-hyperextension means is associated with a different part or parts of the orthosis.

The anti-hyperextension means is preferably adapted to inhibit the lower limb from naturally extending or from hyperextending when the lower limb is positioned on a surface, such as for example, when a subject is supine on a surface, such as a bed. The antihyperextension means, in use, assists in maintaining the lower limb preferably at least 5 degrees flexed from natural extension, and more preferably, from 5 to 15 degrees flexed from natural extension. The invention also envisages the antihyperextension means assisting in maintaining the lower limb in greater degrees of flexion from natural extension, including, for example, 20 to 40 degrees flexed from natural extension.

Preferably, the anti-hyperextension means is adapted so as to substantially maintain the anatomical region adjacent and/or surrounding the bellies of the gastrocnemius and soleus muscles relatively higher than the anatomical region adjacent and/or surrounding the Achilles tendon so that the lower limb is substantially inhibited from naturally extending or from hyperextending.

Preferably, the anti-hyperextension means is provided in the region of a part of the orthosis body substantially opposite the support surface. In some embodiments, the region of a part of the orthosis body substantially opposite the support surface is the base region or in the vicinity of the base region. In one preferred embodiment, the anti-hyperextension means is provided by a portion of the orthosis body which is relatively thick compared to other portions of the orthosis body, so that, for example, a side view of the orthosis reveals that the proximal end portion is relatively thicker than the distal end portion.

In another preferred embodiment, the anti-hyperextension means is provided by the physical configuration of the support surface and a resting surface of the orthosis on which the orthosis rests when placed on a surface, such as an operating theatre table or a bed. Preferably, the resting surface is substantially opposite the support surface. In one such preferred embodiment, the physical configuration of the support surface and the resting surface is provided by an angle between a longitudinal axis of the support surface and a longitudinal axis of the resting surface. Preferably, the angle is such that, in use, the lower limb orthosis inhibits the lower limb from naturally extending or from hyperextending.

In yet another preferred embodiment, the anti-hyperextension means is provided by the physical configuration of the relief region and the resting surface. In one such preferred embodiment, the physical configuration of the relief region and the resting surface is provided by an angle between a longitudinal axis of the relief region and the longitudinal axis of the resting surface. Preferably, the angle is such that, in use, the lower limb orthosis inhibits the lower limb from naturally extending or from hyperextending.

In still yet another preferred embodiment, the anti-hyperextension means is provided by the physical configuration of the relief means and the resting surface, and more particularly, between the physical configuration of a weight-bearing configuration of the relief means and the resting surface. The weight-bearing configuration of the relief means is preferably the configuration adopted by the relief means when a lower limb is resting in or on the orthosis. In one such preferred embodiment, the physical configuration that provides the anti-hyperextension means is provided by an angle between the weight-bearing configuration of the relief means and the longitudinal axis of the resting surface. Preferably, the angle is such that, in use, the lower limb orthosis inhibits the lower limb from naturally extending or from hyperextending.

In an alternative embodiment, the anti-hyperextension means is provided by an elevating member connected to, secured to or integral with the orthosis body. The elevating member of such embodiments can be of any shape and be formed of any material provided that the elevating member is able to provide anti-hyperextension means function as described above.

In another alternative embodiment, the anti-hyperextension means is provided by an inflatable member adapted to be adjacent to, connected to, secured to, or integral with at least a portion of the resting surface. In one such preferred embodiment, the inflatable member is adapted so that upon inflation, a longitudinal axis of the support surface is caused to make an angle with a longitudinal axis of a surface on which the orthosis is resting. Preferably, the angle is such that, in use, the lower limb orthosis inhibits the lower limb from naturally extending or from hyperextending.

In yet another preferred embodiment, the anti-hyperextension means is provided by a combination of any two or more of the above described mechanisms for providing anti-hyperextension means, or by any other mechanism that would provide anti-hyperextension means function as described above.

In a preferred embodiment, the orthosis is a below knee orthosis adapted for use on an underside of the below knee region of the lower limb. Preferably, in use, the orthosis makes no contact with the thigh of the lower limb.

In preferred embodiments, the orthosis is formed of a material, or covered or coated by a material, adapted to be wiped down with one or more cleansing agents including those having one or more properties selected from the group consisting of antiseptic, antimicrobial, microbial growth inhibitor, disinfectant or other cleaning agents. This can contribute to improvement of infection control, particularly where the orthosis is used in the operating theatre or in other healthcare environments.

When the removability, replaceability and/or disposability of some preferred embodiments of the relief means are coupled with the wipe down properties of the material from which some preferred embodiments of the orthosis are formed, the orthosis is suitable for use with the same subject or a plurality of different subjects. After each instance or period of use, a first disposable relief means is discarded, the orthosis is wiped down with a suitable cleansing agent, such as an antiseptic, and a second disposable relief means is received by or secured to the relief region of the orthosis. The orthosis of such embodiments is then ready for use with the same subject or with a different subject.

Some preferred embodiments of the orthosis include one or more straps or other securing means to secure or hold the orthosis to the lower limb. Other preferred embodiments are adapted to provide a support on which the lower limb lies or rests and do not include straps or securing means.

In some preferred embodiments, the orthosis is adapted to support one lower limb. In other preferred embodiments, the orthosis is adapted to support two lower limbs. In some such embodiments, each lower limb has its own respective support surface, relief means and relief region. In other such embodiments, both limbs together share a support surface, relief means and relief region.

In a second aspect, the present invention provides an orthosis comprising:
an orthosis body;
a support surface adapted to support a portion of a subject body part, the support surface connected to, secured to, or integral with the orthosis body;
relief means adapted to relieve a portion of a subject body part from pressure; and
at least one relief region connected to, secured to, or integral with the orthosis body or the support surface or the orthosis body and the support surface, the relief region adapted to receive, secure, or integrate the relief means.

According to a third aspect, the present invention provides an above heel lower limb orthosis comprising:
an orthosis body;
a support surface adapted to support a portion of a lower limb, the support surface connected to, secured to, or integral with the orthosis body;
relief means adapted to relieve a portion of a lower limb from pressure; and
at least one relief region integral with the orthosis body or the support surface or the orthosis body and the support surface, the relief region depressed relative to the support surface and adapted to receive, secure, or integrate the relief means.

According to a fourth aspect, the present invention provides a method of using a lower limb orthosis comprising:
providing an orthosis according to any one of the first or third aspects of the invention; and
removing the relief means from the orthosis and replacing the removed relief means with a further relief means.

In some preferred embodiments of the method of the fourth aspect, following arranging a first relief means to be received by or secured to a relief region of the orthosis, the orthosis is placed with the first relief means on or operably adjacent a subject for use by the subject. After an instance or period of use of the orthosis by the subject, the first relief means is removed. A further relief means is then arranged to be received by or secured to a relief region of the orthosis, and the orthosis with the further relief means is placed on or operably adjacent the subject or a different subject for use of the orthosis, In one preferred embodiment of the method of the fourth aspect of the present invention, the orthosis is wiped down with a suitable cleansing agent, such as an antiseptic, between each instance or period of use.

In other preferred embodiments of the method of the fourth aspect, a set of disposable relief means are used for embodiments of the orthosis with more than one relief region. In such embodiments of the method, the first and further disposable relief means defined in the fourth aspect of the invention are substituted respectively by first and further sets of disposable relief means. Preferably, each disposable relief means from each set of disposable relief means is arranged to suitably be received by or connected to each relief region of the orthosis as defined in the fourth aspect of the invention.

According to a fifth aspect, the present invention provides a method for providing pressure relief to a lower limb of a subject comprising:
placing a lower limb orthosis according to any one of the first or third aspects of the present invention on or operably adjacent the lower limb of the subject.

Preferably, the method is administered so as to reduce the incidence of pressure ulcer formation in the subject when his or her lower limb is positioned on a surface, as is the case, for example, when the subject is supine on a surface, such as a bed. Preferably, the subject's lower limb is supported such that his or her heel and/or ankle remain free of contact with the surface.

In another preferred embodiment of the method of the fifth aspect, the method is administered so as to decrease popliteal vein compression associated with natural extension and/or hyperextension of the knee. Preferably, the method assists in reducing the incidence of deep vein thrombosis in subjects to whom the method is administered.

In another preferred embodiment of the method of the fifth aspect, the method is administered so as to reduce knee pain and/or tenderness associated with reduced lower limb muscle tone in a paralysed, partially paralysed or anaesthetised subject.

In another preferred embodiment of the method of the fifth aspect, the method is administered so as to reduce knee pain and/or tenderness associated with strain on knee ligaments.

According to a sixth aspect, the present invention provides a method for providing pressure relief to a living body part of a subject comprising:
placing an orthosis according to the second aspect of the present invention on or operably adjacent the living body part of the subject.

According to a seventh aspect, the present invention provides a method of reducing knee pain and/or tenderness in a subject, comprising:
placing a lower limb orthosis according to any one of the first or third aspects of the present invention on or operably adjacent the lower limb of the subject.

In one preferred embodiment, the knee pain and/or tenderness is associated with reduced lower limb muscle tone. In another preferred embodiment, the reduced lower limb muscle tone is associated with strain on knee ligaments.

In preferred embodiments, the method of the fifth, sixth or seventh aspects is administered to a subject who has been medically anaesthetised and/or medically paralysed or who has muscle weakness, a physical disability, or paralysis due to some other cause, such as spinal cord injury, or who is experiencing prolonged bed-rest or immobility.

In some preferred embodiments, the method is of the fifth, sixth or seventh aspects is administered before, during or after an operative procedure or a combination of these.

According to an eighth aspect, the present invention provides a body part resting surface for placement on, in association with, or in operable engagement with, a support member, comprising:
a support surface adapted to support a portion of a body part;
relief means adapted to relieve a portion of a body part from pressure; and
at least one relief region adapted to receive, secure, or integrate the relief means.

In some preferred embodiments, the at least one relief region is connected to, secured to, or integral with the support surface.

Preferably, the support member is an orthosis, a bed, a mattress, an operating theatre table, a calliper, a block or wedge or any other device that provides a resting or support surface for a body part of a subject.

In a particularly preferred embodiment, the body part supported by the support surface is a lower limb.

Operable engagement of the body part resting surface with the support member can be effected by any suitable means including, without limitation, with double-sided adhesive, Velcro, glue, screws or other similar such securing means, or by mounting or resting the body part resting surface on or in operable association with the support member, for example.

Preferred embodiments of each of the support surface, relief means, and relief region and of the physical relationship or configuration of two or more of these may include one or more of the features identified above in the specification with respect to the orthoses of the first, second or third aspects of the invention.

In some preferred embodiments of the eighth aspect, the body part resting surface further includes a further support surface and/or further relief means and/or further corresponding at least one relief region. In some such embodiments, the body part resting surface is adapted to be used to support two or more body parts, such as, for example, two or more limbs.

According to a ninth aspect, the present invention provides a relief means adapted to be received by, connected to, secured to, or integrated with, an orthosis having a relief region adapted to accommodate the relief means.

According to a tenth aspect, the present invention provides a relief means when used with an orthosis which has a relief region adapted to accommodate the relief means.

In some preferred embodiments of the relief means of the ninth or tenth aspects of the invention, the orthosis is according to any one of the first, second or third aspects of the invention.

Preferred embodiments of the relief means of the ninth or tenth aspects may include one or more of the features identified for the relief means of the orthoses of the first, second or third aspects of the invention. Alternative embodiments of the relief means of the ninth or tenth aspects may include other features that enable the relief means to relieve at least a portion of a body part from pressure or discomfort.

In an eleventh aspect, the present invention provides a relief means adapted to be received by, connected to, secured to, or integrated with an orthosis, the orthosis comprising:
 an orthosis body;
 a support surface adapted to support a portion of a lower limb, the support surface connected to, secured to, or integral with the orthosis body; and
 at least one relief region connected to, secured to, or integral with the orthosis body or the support surface or the orthosis body and the support surface, the relief region depressed relative to the support surface and adapted to receive, secure, or integrate the relief means.

According to a twelfth aspect, the present invention provides a relief means adapted to be received by, connected to, secured to, or integrated with a relief region in a body part resting surface, the body part resting surface comprising:
 a support surface adapted to support a portion of a body part; and
 at least one relief region adapted to receive, secure, or integrate the relief means.

According to a thirteenth aspect, the present invention provides an orthosis comprising:
 an orthosis body;
 at lease one support surface adapted to support a portion of at least one body part, each support surface connected to, secured to, or integral with the orthosis body;
 at least one relief means adapted to relieve a portion of at lease one body part from pressure; and
 at least one relief region connected to, secured to, or integral with the orthosis body or one or more support surface/s or the orthosis body and one or more of the support surface/s, each relief region adapted to receive, secure, or integrate at least one relief means.

In some preferred embodiments of the orthosis of the eleventh aspect, the orthosis is adapted to support the two lower limbs of a subject. In some such embodiments, each lower limb has its own respective support surface, relief means and relief region. In other such embodiments, both limbs together share a support surface, relief means and relief region. Persons skilled in the art would appreciate that other permutations and combinations of the support surface/s, relief means (or plurality of relief means) and relief region/s may be suitable depending on the particular circumstances to which the orthosis is to be applied.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention.

In order that the present invention may be more clearly understood, preferred embodiments will be described with reference to the following drawings and examples.

DETAILED DESCRIPTION OF PREFERRED EMBODIMENTS

Figure 1:
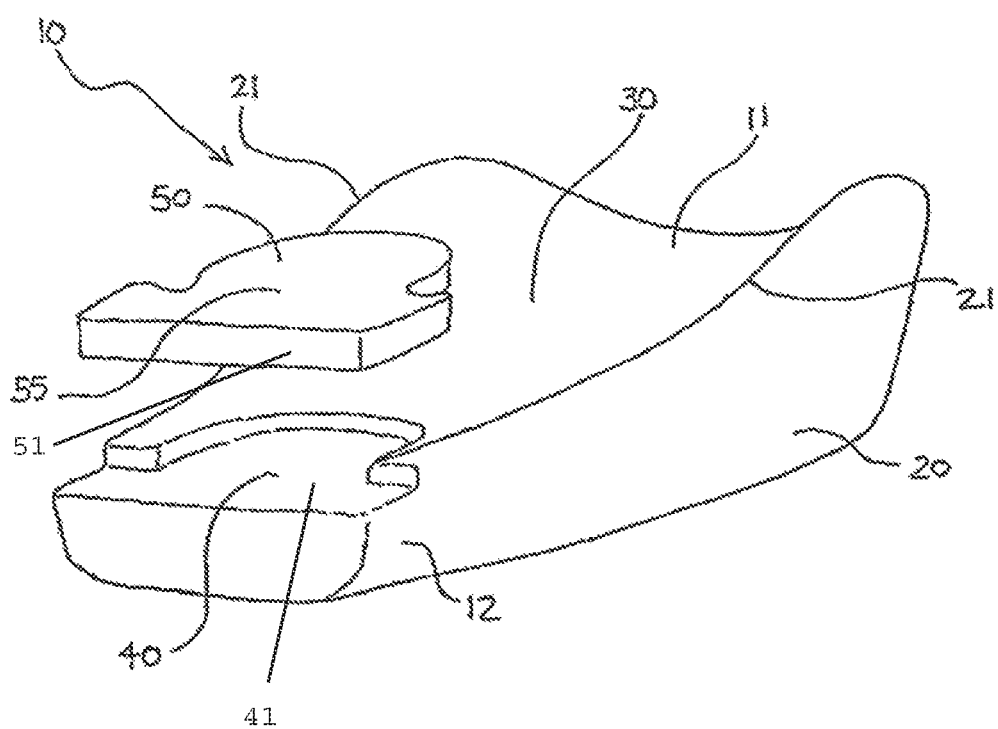
FIG. 1 is a perspective view of a lower limb orthosis according to a preferred embodiment of the present invention, along with a correspondingly shaped relief means adapted for connecting to, securing to, or integrating with, the orthosis.
Figure 2:
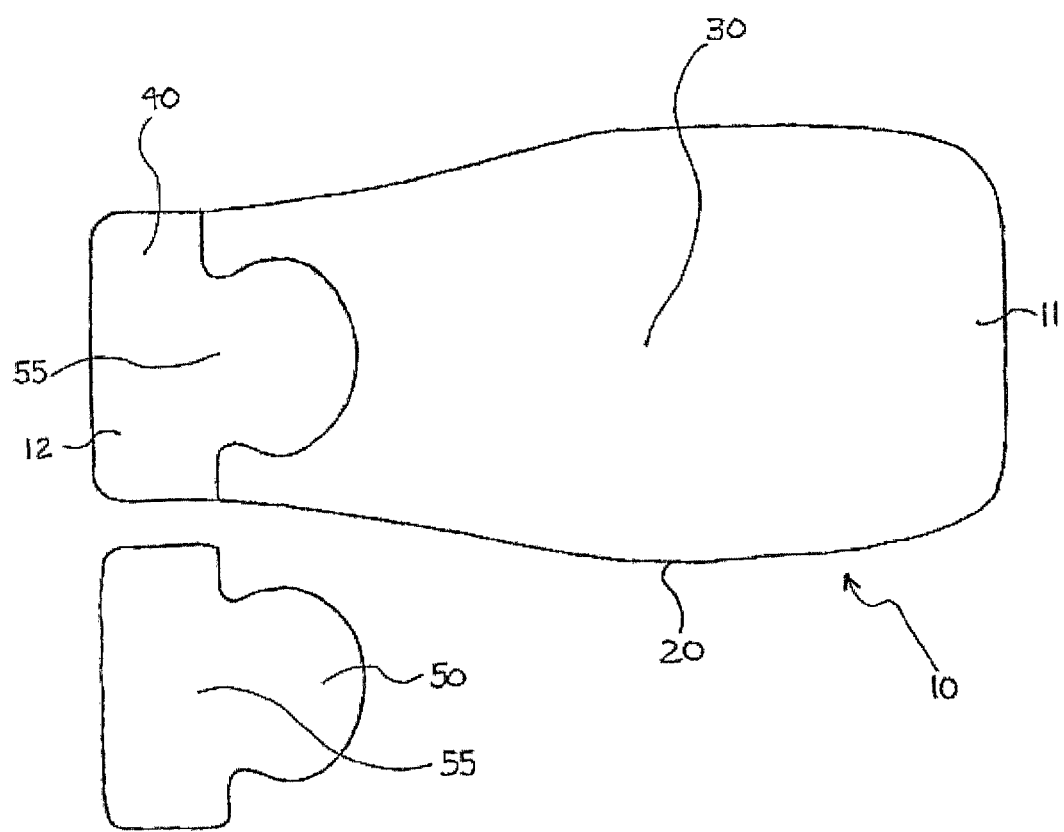
FIG. 2 is a top view of the lower limb orthosis depicted in FIG. 1, along with a top view of the correspondingly shaped relief means.
Figure 3:
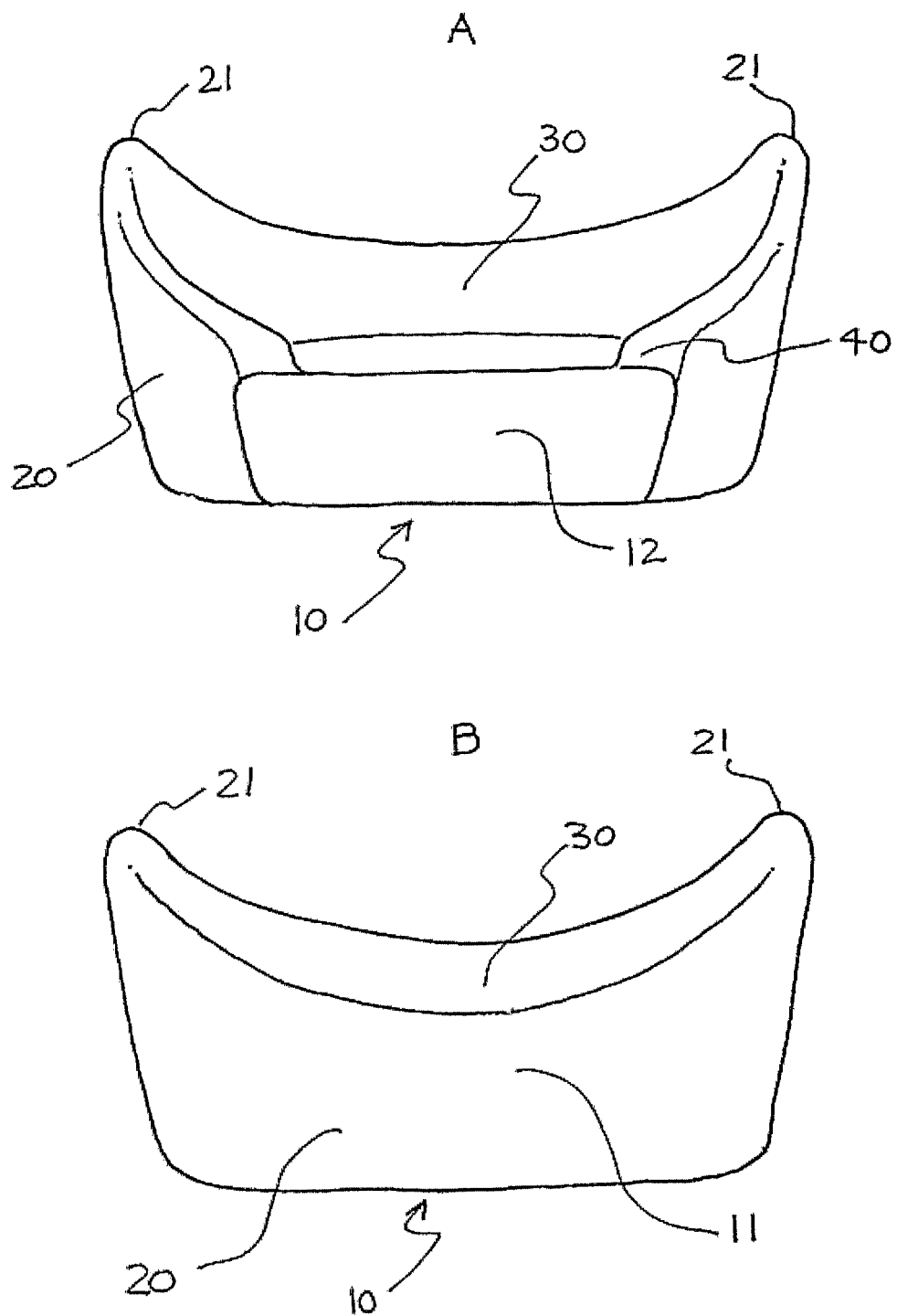
FIG. 3A is a front view of the orthosis depicted in FIG. 1.
FIG. 3B is a rear view of that orthosis.
Figure 4:
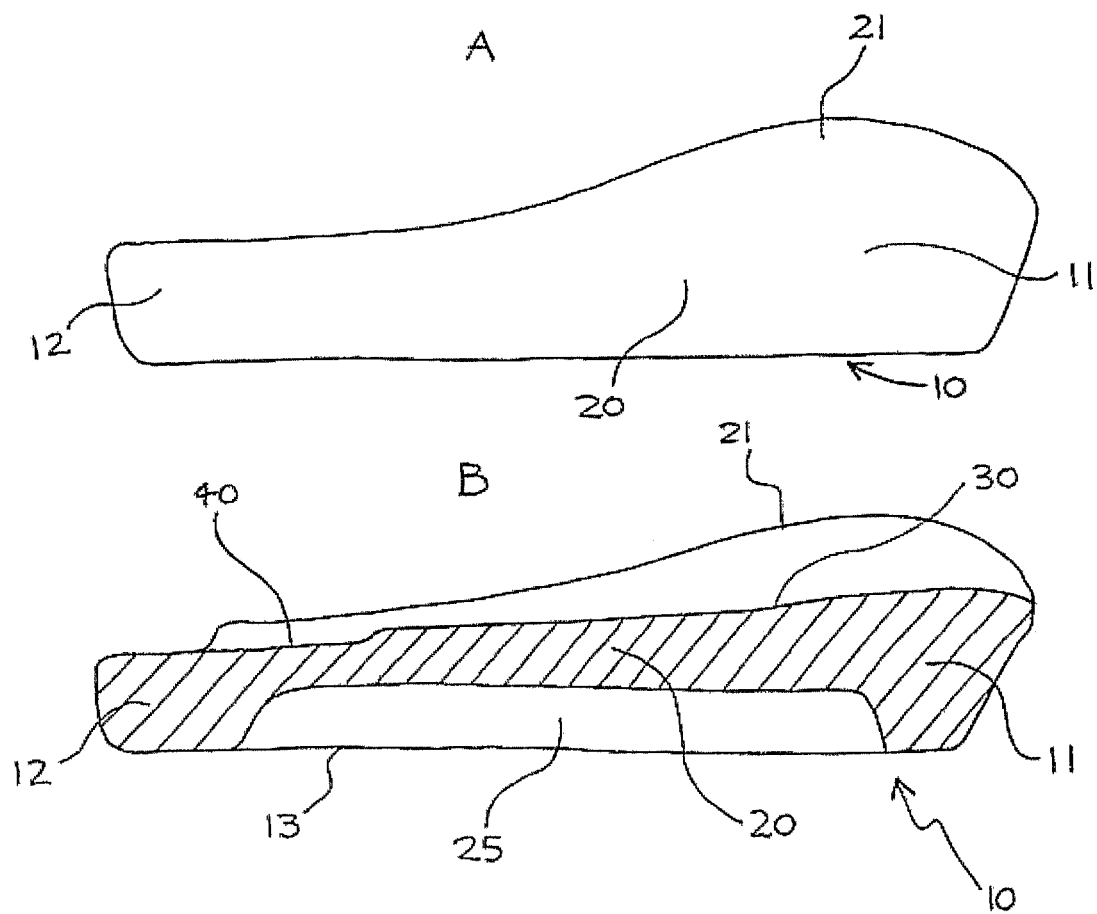
FIG. 4A is a side view of the orthosis depicted in FIG. 1.
FIG. 4B is a sectional side view of the orthosis depicted in FIG. 1, illustrating various segments of the orthosis.

In this specification:

The term "naturally extending" (and grammatical variations of this term) when used in relation to the lower limb means the extended or outstretched position in which the lower limb would naturally rest when extended on a surface, such as when the subject is lying supine on the surface, or is sitting with his or her lower limb naturally outstretched on the surface. The position may differ from subject to subject, may vary depending on the degree of muscle tone present in the lower limb/s, and may be different for each of a subject's lower limbs.

The term "hyperextended" (and grammatical variations of this term) when used in relation to the lower limb means extended beyond natural extension. By way of example only, during operative procedures wherein the subject is supine, a block is often placed under the subject's Achilles tendon in order to prevent the formation of pressure ulcers in the vicinity of the ankle, including on or around the calcaneus and lateral malleolus. Placing the block as such gives rise to hyperextension of the knee.

The term "above heel" (and grammatical variations of this term) when used in relation to an orthosis means that the orthosis, in use, is located generally at or above the heel of a subject. Preferred embodiments of an above heel orthoses of the present invention are not suitable for use as an instep in a shoe or for otherwise supporting the sole of a subject's foot.

Preferred embodiments of the orthosis of the present invention take the form of an above heel lower limb orthosis 10 as depicted in the Figures. The lower limb orthosis 10 comprises:

an orthosis body 20;

a support surface 30 adapted to support a portion of a lower limb, the support surface 30 connected to, secured to, or integral with the orthosis body 20;

relief means 50 adapted to relieve a portion of a lower limb from pressure; and at least one relief region 40 connected to, secured to, or integral with the orthosis body 20 or the support surface 30 or the orthosis body 20 and the support surface 30, the relief region 40 adapted to receive, secure, or integrate, the relief means 50.

FIGS. 1 to 5 illustrate one preferred embodiment of the lower limb orthosis 10 of the present invention.

In this embodiment, the orthosis body 20 includes wing members 21 which create a channel adapted to receive the support surface 30 and which can help to inhibit the lower limb from dislodging or rolling-off the orthosis 10 in use. The support surface 30 is smooth and uniform and is shaped so as to receive the anatomical region adjacent and/or surrounding the bellies of the gastrocnemius and soleus muscles. The support surface 30 is to be connected to or secured to the orthosis body 20 in this embodiment.

The relief region 40 is integral with the orthosis body 20 in this embodiment. The relief region 40 is located on the orthosis body in a region where, in use, the orthosis 10 supports the anatomical region adjacent and/or surrounding the Achilles tendon of the lower limb. The relief region 40 has a support floor 41 which is depressed relative to the 30 support surface 30 and has a shape, or a portion of its shape, which corresponds to a portion of the shape of the relief means 50.

The relief means 50 has a composite shape comprising a part-circle, greater in area than a semi-circle with the same diameter, adjacent a long side of a rectangle. The points at which the circumference of the part-circle meet the long side of the rectangle are curved so that the top view of the relief means 50 (as particularly well illustrated in FIG. 2) is a seamless composite shape. The diameter of the part-circle is lesser in size than the length of the long side of the rectangle.

The relief means 50 includes a relief surface 55 and an end wall 51. In use, the relief surface 55 and the support surface 30 substantially contour an underside of the lower limb, particularly, the anatomical regions adjacent and/or surrounding the bellies of the gastrocnemius and soleus muscles and the Achilles tendon. The relief means 50 encloses pressure relief content comprised, in this embodiment, of gel.

Figure 5:
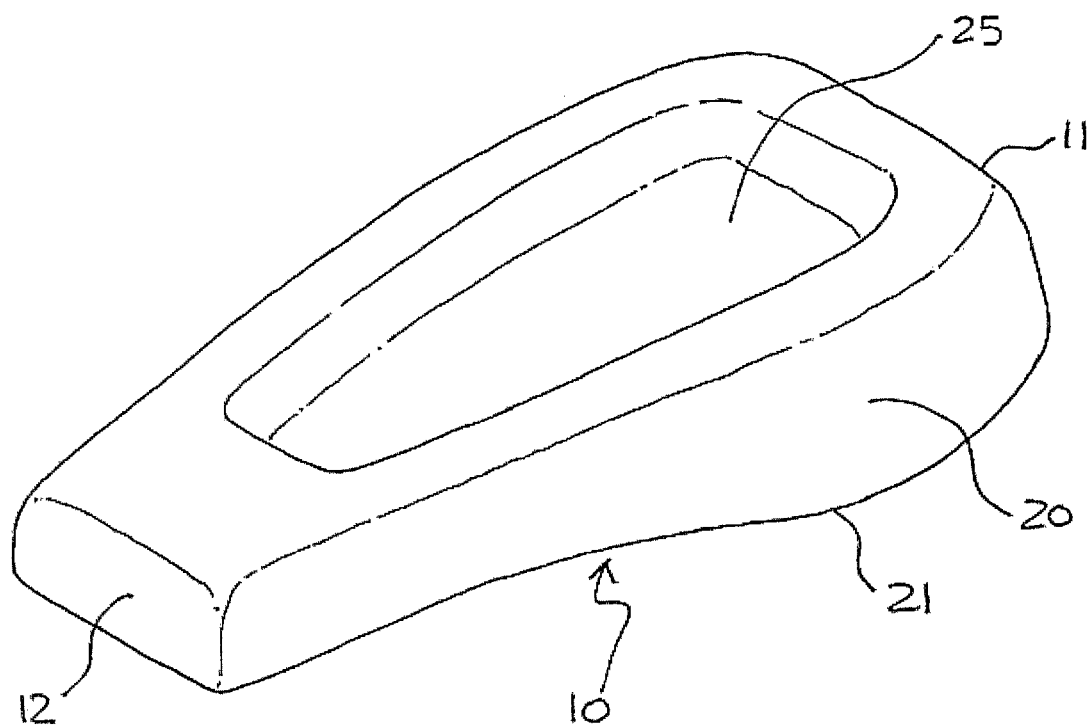
FIG. 5 is a bottom perspective view of the orthosis depicted in FIG. 1.

As is illustrated well in FIG. 5, the orthosis body 20 includes a hollowed portion 25 in the region or area of a resting surface 13 which, in use, may rest on a surface, such as a bed or operating theatre table. The hollowed portion 25 reduces the volume of material required in the manufacture of the orthosis 10 according to this embodiment.

The orthosis 10 of this embodiment also includes anti-hyperextension means adapted to prevent the lower limb from naturally extending or hyperextending when the orthosis 10 is in use on a surface. In this embodiment, the anti-hyperextension means is provided by the physical configuration of the support surface 30 and the resting surface 13 of the orthosis 10. The physical configuration of the relevant parts of these surfaces 30, 13 are illustrated in FIG. 4B, which illustrates an angle between a longitudinal axis of the support surface 30 and a longitudinal axis of the resting surface 13.

Also, it can be seen in FIG. 4B that the thickness of the orthosis body 20 from proximal end portion 11 to distal end portion 12 varies. The angle discussed above between the longitudinal axis of the support surface 30 and the longitudinal axis of the resting surface 13 is also provided by virtue of the varying thickness of the orthosis body 20 as shown in FIG. 4B. As can be appreciated, the proximal end portion 11 of the orthosis body is thicker than the distal end portion 12. This also aids in the provision of the anti-hyperextension means.

A further preferred embodiment of the lower limb orthosis 10 of the invention is illustrated in FIGS. 6 to 10.

Figure 6:
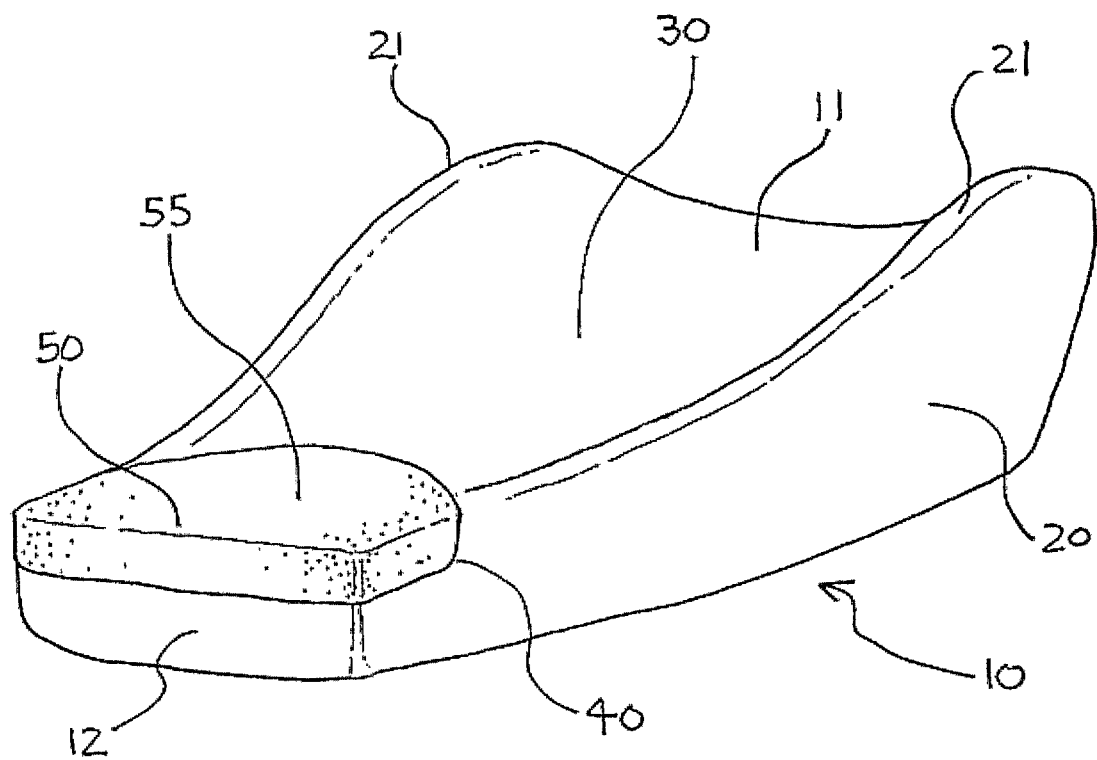
FIG. 6 is a perspective view of a lower limb orthosis of a further preferred embodiment of the present invention, along with a relief means received by, secured to, or integrated with, the relief region.
Figure 7:
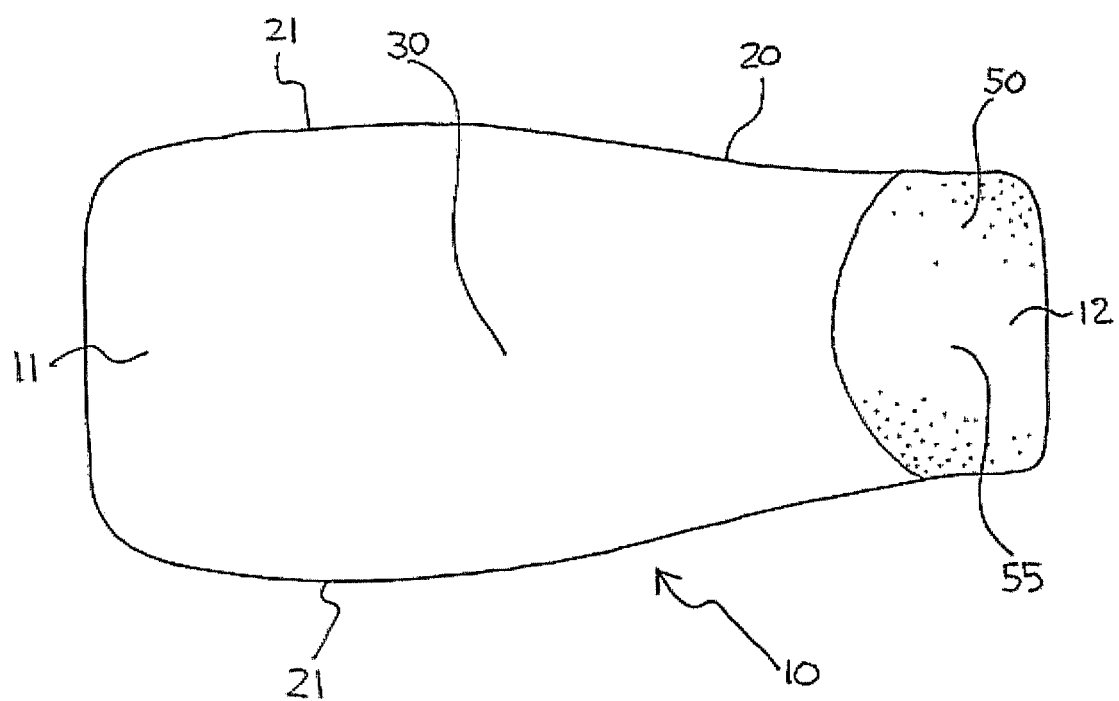
FIG. 7 is a top view of the orthosis depicted in FIG. 6.
Figure 8:
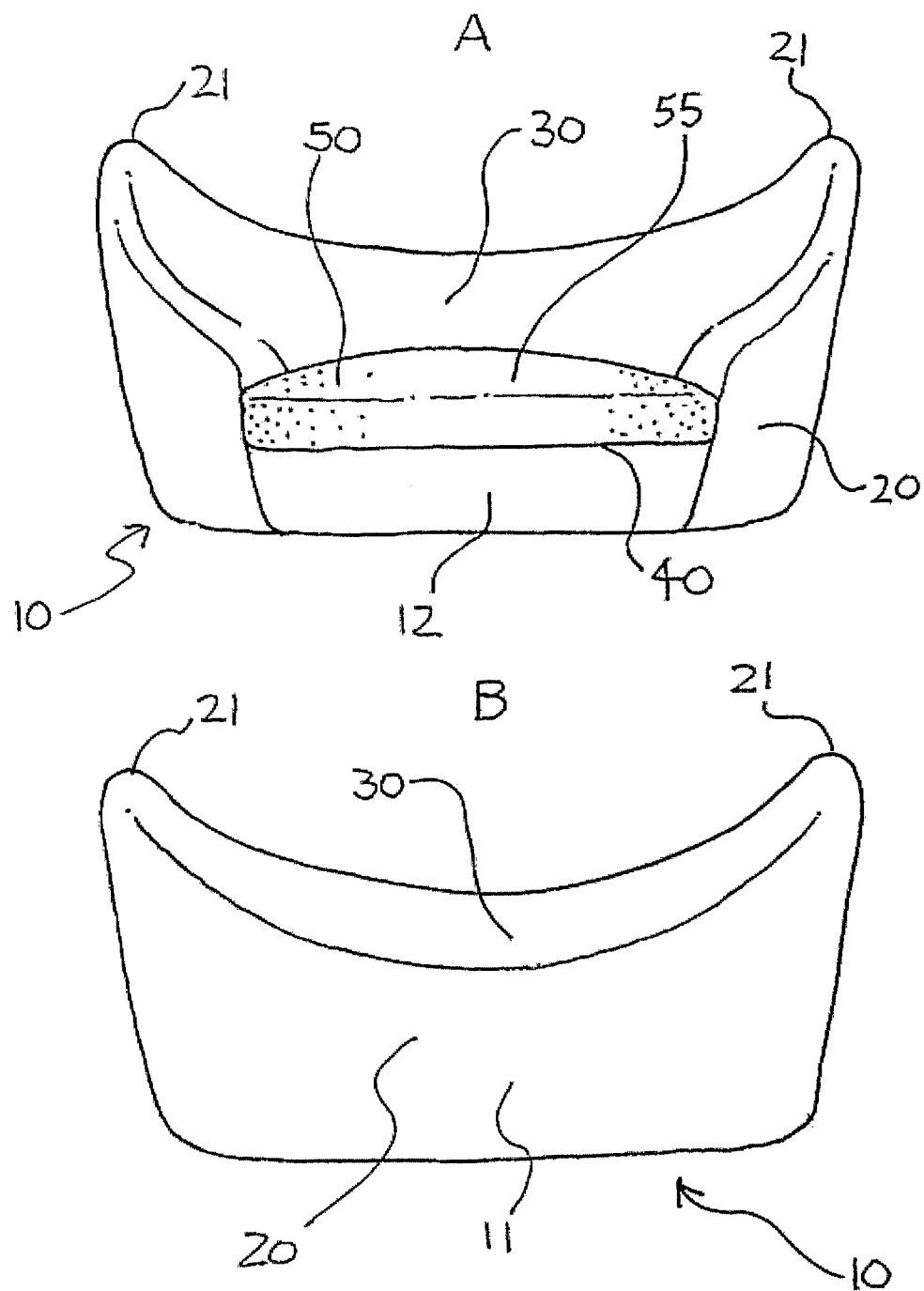
FIG. 8A is a front view of the orthosis depicted in FIG. 6
FIG. 8B is a rear view of that orthosis.
Figure 9:
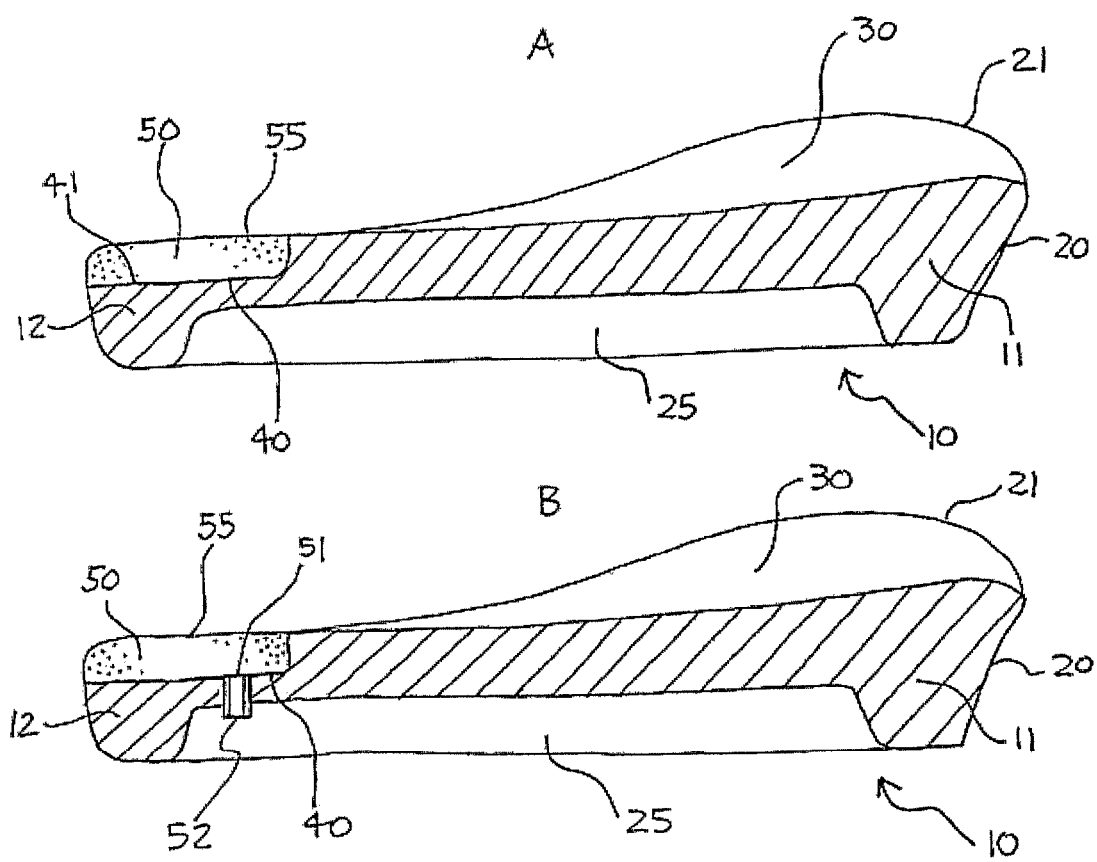
FIG. 9A is a sectional side view of one embodiment of the orthosis depicted in FIG. 6 illustrating various segments of the orthosis.
FIG. 9B is a sectional side view of a further embodiment of the orthosis depicted in FIG. 6 illustrating various segments of the orthosis.
Figure 10:
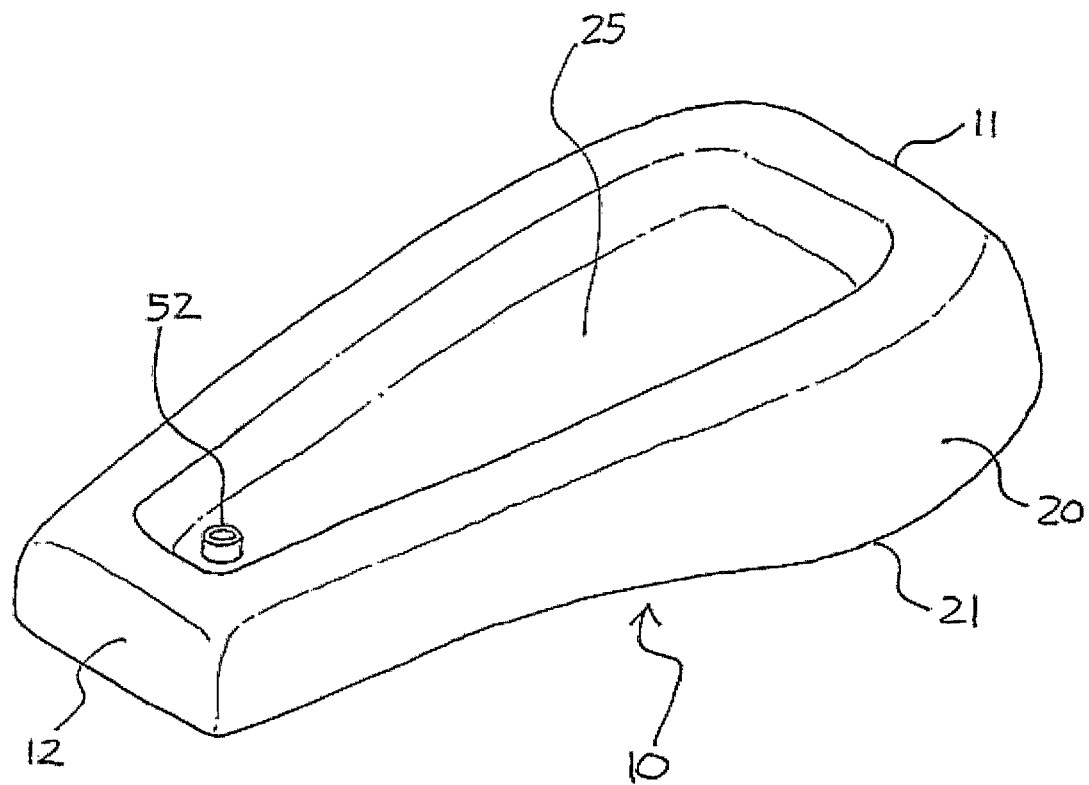
FIG. 10 is a bottom perspective view of the embodiment of the orthosis depicted in sectional side view in FIG. 9B.

Referring first to FIG. 6, the preferred embodiment of the orthosis 10 depicted in this Figure is somewhat similar in shape and/or configuration to the preferred embodiment depicted in FIG. 1. One difference is in the shape and/or configuration of the relief means 50. Also to be noted is the relief means 50 is illustrated as received by, secured to, or integral with, the orthosis body 20 in the embodiment depicted in FIGS. 6 to 10.

The remainder of the description of the embodiment depicted in FIGS. 6 to 10 refers specifically to these different features, as the similar features have already been previously described for the embodiment depicted in FIGS. 1 to 5.

FIGS. 9A and 9B provide sectional side views of two different configurations for this preferred embodiment of the orthosis 10.

FIG. 9A illustrates the relief means 50 integrated with the orthosis body 20 in the vicinity of the distal portion 12. In one such arrangement, relief region wall 41 provides a lower containment surface of the relief means 50 and relief surface 55 provides the upper containment surface of the relief means 50. The pressure relief content is contained between the relief region wall 41 and an underside of relief surface 55.

In another such arrangement, the relief means 50 is in the form of an enclosed pocket and is adapted to integrate with, connect to or be received by the relief region 40. FIG. 9B illustrates an alternative configuration in which the relief means 50 includes a closable opening 51 in communication with relief means nozzle 52. Pressure relief content can be allowed or expelled by movement through the relief means nozzle 52. In this embodiment, relief region 40 includes an aperture (not shown) which is adapted to receive the relief means nozzle 52. The aperture extends through the orthosis body 20 and opens into hollowed portion 55. Access to the relief means nozzle 52, and consequent ability to regulate the volume of pressure relief content within relief means 50, is gained via hollowed portion 25 as is well illustrated in FIG. 10.

In one such arrangement, the relief means 50 can be secured to the relief region 40 when a clipping means (not shown) holds the relief means nozzle 52 in position in the region of its extension through the opening of the aperture into hollowed portion 25. In an alternative arrangement, relief means 52 or another extendable member (not shown) may be sized so as to expand when extending out of the opening of the aperture (not shown) into hollowed portion 25 so as to act as a lug locking or securing the relief means 50 in place.

Figure 11:
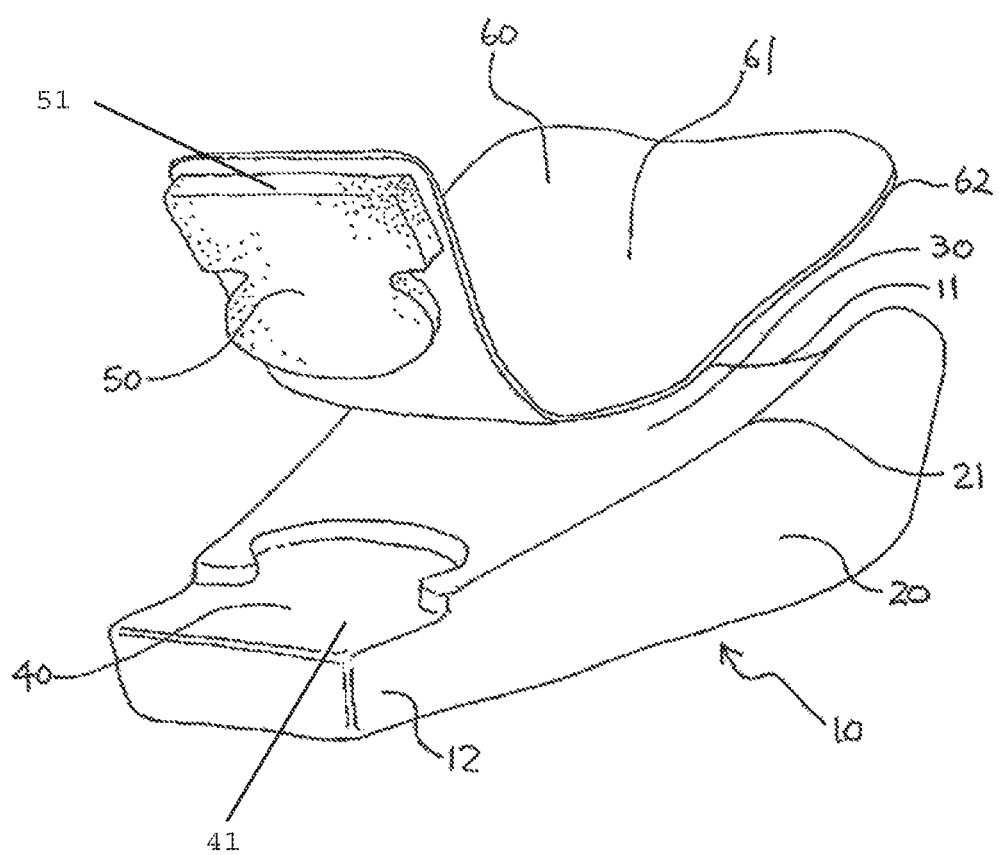
FIG. 11 is a perspective view of a lower limb orthosis according to a preferred embodiment of the present invention, along with a correspondingly shaped relief means adapted for connecting to, securing to, or integrating with, the orthosis. The relief means includes a liner element.

Many features of the embodiment of the orthosis 10 depicted in FIG. 11 are similar to those features of the embodiment depicted in earlier figures. The description of this FIG. 11 focuses on relief means 50 which includes a liner element 60.

The liner element 60 of this embodiment is secured to relief means 50. As can be appreciated, in this embodiment, the liner element 60 substantially lines or covers relief surface 55 (not shown in this figure) of relief means 50 and extends away from relief means 50 thereby providing a flap-like structure 62 for substantially lining or covering other parts of the orthosis 10, such as the support surface 30 as depicted. In use, liner element surface 61 contacts the underside of the lower limb (not shown).

Figure 12:
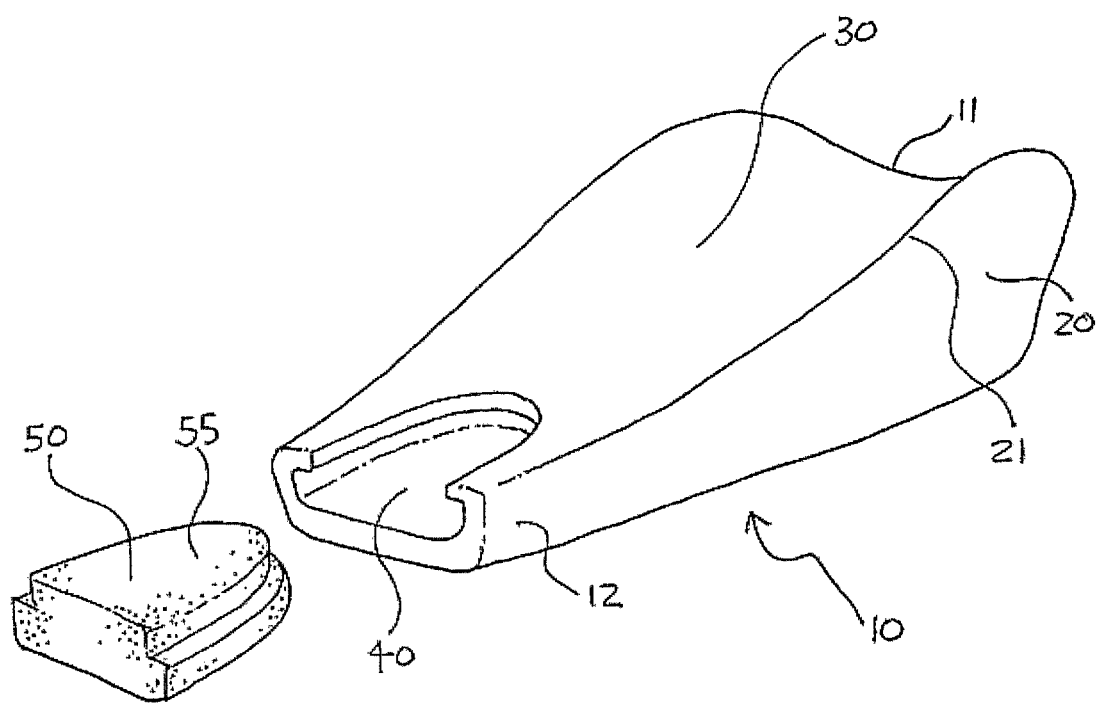
FIG. 12 is a perspective view of a lower limb orthosis according to a preferred embodiment of the present invention, along with a correspondingly shaped relief means adapted for slot-insertion into the orthosis.
Figure 13:
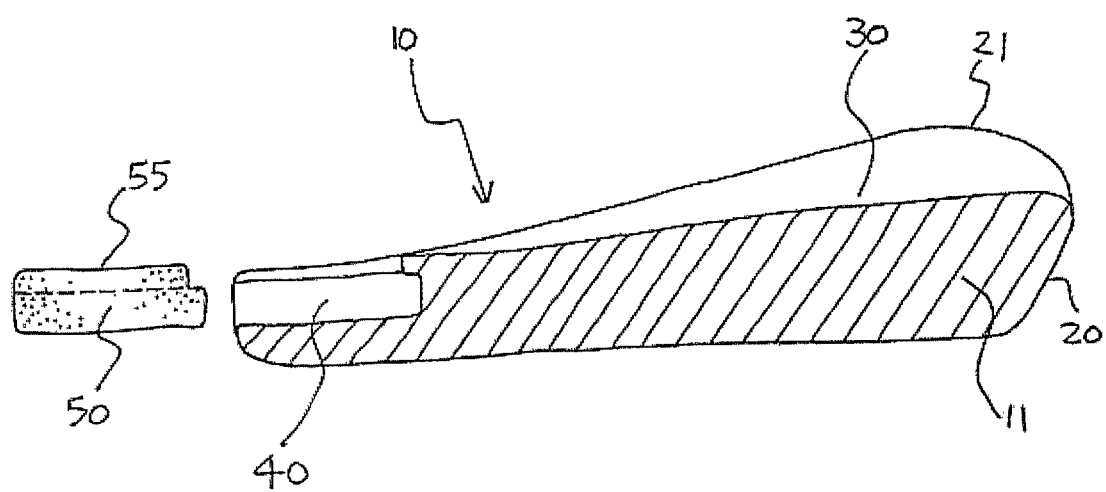
FIG. 13 is a sectional side view of one embodiment of the orthosis depicted in FIG. 12 illustrating various segments of the orthosis.

FIGS. 12 and 13 illustrate different views of yet another preferred embodiment of the orthosis 10. In this embodiment, relief means 50 is adapted to be inserted into a substantially correspondingly shaped slot-type structure formed in an end 12 of the orthosis body 20 and the relief region 40.

The relief means 50 of the embodiments described above is disposable in some preferred embodiments. Further, the orthosis 10 is formed of a material, or covered or coated by a material, adapted to be wiped down with one or more cleansing agents including those having one or more properties selected from the group consisting of antiseptic, antimicrobial, microbial growth inhibitor, disinfectant or other cleaning agents.

The orthosis 10 of some preferred embodiments is well suited to be used with the same subject or a plurality of different subjects. After each instance or period of use, a first disposable relief means 50 is discarded, the orthosis 10 is wiped down with a suitable cleansing agent, such as an antiseptic, and a second disposable relief means 50 is received by or secured to the relief region 40 of the orthosis 10. The orthosis 10 of such embodiments is then ready for use with the same subject or with a different subject.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An above heel lower limb orthosis comprising:
    an orthosis body having a proximal end thicker than a distal end that is configured to maintain a user's anatomical region adjacent the bellies of the gastrocnemius and soleus muscles higher than the user's anatomical region adjacent the Achilles tendon to inhibit hyperextension of a lower limb of a subject;
    a support surface adapted to support a portion of a user's lower limb and configured to inhibit hyperextension of a user's knee, the support surface connected to, secured to, or integral with the orthosis body and which is configured to extend from a point adjacent and distal the popliteal fossa to adjacent and proximal to a user's Achilles tendon and does not apply pressure to the anatomical region adjacent or surrounding the user's popliteal fossa so as not to occlude the user's popliteal vein;
    at least one relief region connected to, secured to, or integral with at least one of the orthosis body or the support surface at the distal end of the orthosis body, the relief region including a support floor which is depressed relative to the support surface and adapted to receive or secure a removable relief pad on the support floor, the removable relief pad adapted to relieve the Achilles tendon portion of a user's lower limb from pressure;
    wherein the relief pad comprises an end wall exposed at the distal end of the orthosis body to facilitate removal of the removable relief pad.

2. The lower limb orthosis of claim 1 wherein the relief region is integral with at least one of the orthosis body or the support surface.

3. The lower limb orthosis of claim 1 wherein the relief pad is formed of one or more materials selected from the group consisting of low density foam, high density foam, open cell and closed cell foams, rubber, solid or semi-solid gels and a combination of two or more thereof.

4. The lower limb orthosis of claim 1 wherein the support surface of the orthosis body has a concave arcuate cross-section configured to support the user's lower limb.

5. The lower limb orthosis of claim 1, wherein the removable relief pad is replaceable with a further removable relief pad.

6. The lower limb orthosis of claim 1 wherein the relief pad is received by or secured to the relief region of the orthosis by double sided adhesive.

7. The lower limb orthosis of claim 1 wherein the relief pad has a shape or configuration which substantially corresponds to a shape or configuration of at least a portion of the relief region of the orthosis.

8. The lower limb orthosis of claim 1 wherein the relief pad is formed into a composite shape consisting of a rectangle adjacent a semi-circle or a rectangle adjacent a part-circle, greater in area than a semi-circle with the same diameter as the part-circle.

9. The lower limb orthosis of claim 8 wherein the semi-circle or part-circle is adjacent to a short side of the rectangle or is adjacent to a long side of the rectangle.

10. The lower limb orthosis of claim 8 wherein the meeting points between a perimeter of the rectangle and a circumference of the semi-circle or part-circle is smooth and curved.

11. The lower limb orthosis of claim 8 wherein the composite shape comprises a rectangle and a part-circle, greater in area than a semi-circle with the same diameter as the part-circle, and
    wherein the part-circle is adjacent the long side of the rectangle, the diameter of the part-circle is shorter than the long side of the rectangle, and the meeting point of the circumference of the part-circle with the long side of the rectangle is smooth and curved.

12. The lower limb orthosis of claim 1 formed of a material, or covered or coated by a material, adapted to be wiped down with one or more cleansing agents including those having one or more properties selected from the group consisting of antiseptic, antimicrobial, microbial growth inhibitor, disinfectant or other cleaning agents.

13. A relief pad adapted to be received by, connected to, or secured to an above heel lower limb orthosis according to claim 1, wherein the relief pad has a shape or configuration that substantially corresponds to a shape or configuration of at least a portion of the relief region of the orthosis body of the above heel lower limb orthosis.

14. The relief pad of claim 13 formed of one or more materials selected from the group consisting of low density foam, high density foam, open cell and closed cell foams, rubber, solid or semi-solid gels and a combination of two or more thereof.

15. The relief pad of claim 13 formed into a composite shape consisting of a rectangle adjacent a semi-circle or a rectangle adjacent a part-circle, greater in area than a semi-circle with the same diameter as the part-circle.

16. The relief pad of claim 15, wherein the semi-circle or part-circle is adjacent to a short side of the rectangle or is adjacent to a long side of the rectangle.

17. The relief pad of claim 15, wherein meeting points between a perimeter of the rectangle and a circumference of the semi-circle or part-circle is smooth and curved.

18. The relief pad of claim 15, wherein the composite shape comprises a rectangle and a part-circle, greater in area than a semi-circle with the same diameter as the part-circle, and
wherein the part-circle is adjacent the long side of the rectangle, the diameter of the part-circle is shorter than the long side of the rectangle, and the meeting point of the circumference of the part-circle with the long side of the rectangle is smooth and curved.

19. A method for providing pressure relief to a lower limb of a subject to inhibit hyperextension of a knee of the subject, the method comprising:
placing the orthosis according to claim 1 on or operably adjacent to the subject's lower limb where the orthosis is configured to inhibit hyperextension of the subject's knee.

* * * * *